(12) United States Patent
Cazares et al.

(10) Patent No.: US 8,036,735 B2
(45) Date of Patent: Oct. 11, 2011

(54) SYSTEM FOR EVALUATING PERFORMANCE OF AN IMPLANTABLE MEDICAL DEVICE

(75) Inventors: Shelley M. Cazares, Washington, DC (US); Haresh G. Sachanandani, Shoreview, MN (US); Benjamin Ettori, Pittsburgh, PA (US); Dan Li, Shoreview, MN (US); Yanting Dong, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1081 days.

(21) Appl. No.: 11/835,812

(22) Filed: Aug. 8, 2007

(65) Prior Publication Data

US 2009/0043355 A1 Feb. 12, 2009

(51) Int. Cl.
*A61B 5/044* (2006.01)
*A61B 5/0452* (2006.01)
(52) U.S. Cl. .................. 600/523; 600/510; 600/522
(58) Field of Classification Search ............. 600/510, 600/522–525
See application file for complete search history.

(56) References Cited

U.S. PATENT DOCUMENTS

| | | | |
|---|---|---|---|
| 5,509,927 A | 4/1996 | Epstein et al. | |
| 2002/0099302 A1* | 7/2002 | Bardy | 600/510 |
| 2006/0135875 A1* | 6/2006 | Crosby et al. | 600/509 |

OTHER PUBLICATIONS

"Insignia I Ultra, Models 1190/1290/1291, Multiprogrammable Pacemakers, System Guide", *Guidant*, (2003),6 pgs.
Obuchowski, N. A., "Receiver operating characteristic curves and their use in radiology", *Radiology 229* (1), PMID 14519861,(2003),3-8.
Zweig, M. H., et al., "Receiver-operating characteristic (ROC) plots: a fundamental evaluation tool in clinical medicine", *Clinical chemistry 39*(8), PMID 8472349,(1993),561-577.

* cited by examiner

*Primary Examiner* — Carl H. Layno
*Assistant Examiner* — Tammie K Heller
(74) *Attorney, Agent, or Firm* — Schwegman, Lundberg & Woessner, P.A.

(57) ABSTRACT

A system evaluates the performance of an implantable medical device, such as by using a remote external server and a user interface and stored historical physiological data of a population of congestive heart failure (CHF) patients. A processor is coupled to a patient data storage device to apply multiple algorithm variations against the same implantable physiological data from the patient to produce corresponding resulting CHF indicators. The user interface includes a display that is configured to display to a user information allowing comparison between the resulting CHF indicators from the multiple algorithm variations. The display also includes a population data selector to permit the user to select physiological data from a population that includes a different set of one or more patients or physiological data collected over a period of time from the patient. This permits optimization of an algorithm parameter or selection of a best performing algorithm.

23 Claims, 6 Drawing Sheets

|   | A |   |   |   | B |   |   |   | C |   |   |   | C' |   |
|---|---|---|---|---|---|---|---|---|---|---|---|---|---|---|
| TP=63 | FP=28 | 91 | | TP=77 | FP=77 | 154 | | TP=24 | FP=88 | 112 | | TP=88 | FP=24 | 112 |
| FN=37 | TN=72 | 109 | | FN=23 | TN=23 | 46 | | FN=76 | TN=12 | 88 | | FN=12 | TN=76 | 88 |
| 100 | 100 | 200 | | 100 | 100 | 200 | | 100 | 100 | 200 | | 100 | 100 | 200 |

A  
TPR = 0.63  
FPR = 0.28  
ACC = 0.68

B  
TPR = 0.77  
FPR = 0.77  
ACC = 0.50

C  
TPR = 0.24  
FPR = 0.88  
ACC = 0.18

C'  
TPR = 0.88  
FPR = 0.24  
ACC = 0.82

*FIG. 8*

SYSTEM FOR EVALUATING PERFORMANCE OF AN IMPLANTABLE MEDICAL DEVICE

TECHNICAL FIELD

This document pertains generally to an implantable medical device, and more particularly, but not by way of limitation, to a system for evaluating the performance of an implantable medical device.

BACKGROUND

Implantable medical devices normally include a processor that executes an algorithm that controls the operation of the implantable medical device. For some implantable medical devices, the operation of the implantable medical device can be altered by either changing the algorithm code of the implantable medical device, or changing the values of parameters that the algorithm code uses during execution. These alterations can be performed via a telemetry link between the implantable medical device and a programmer.

OVERVIEW

A system evaluates the performance of an implantable medical device, such as by using a remote external server and a user interface and stored historical physiological data of a population of congestive heart failure (CHF) patients. A processor is coupled to a patient data storage device to apply multiple algorithm variations against the same implantable physiological data from the patient to produce corresponding resulting CHF indicators. The user interface includes a display that is configured to display to a user information allowing comparison between the resulting CHF indicators from the multiple algorithm variations. The display also includes a population data selector to permit the user to select physiological data from a population that includes a different set of one or more patients or physiological data collected over a period of time from the patient. This permits optimization of an algorithm parameter or selection of a best performing algorithm.

Example 1 describes a system for use with an implantable medical device, the system comprising a remote external server comprising a physiological data input, configured to receive physiological data into a patient data storage device that stores historical physiological data of a population of congestive heart failure (CHF) patients, the physiological data input comprising an implantable physiological data input configured to receive implantable physiological data from an implantable physiological sensor of a first patient; a processor, coupled to the patient data storage device, the processor configured to apply multiple algorithm variations against the same implantable physiological data from the first patient to produce corresponding resulting CHF indicators; and a local or remote external user interface, configured to be coupled to the remote external server using a communications network, the user interface comprising a display, configured to display to a user information allowing comparison between the resulting CHF indicators from the multiple algorithm variations, and the display including a population data selector configured to permit the user to select physiological data from a population comprising a different set of one or more patients or physiological data collected over a period of time from the first patient, thereby further allowing an optimization of an algorithm parameter or a selection of a best performing algorithm.

In Example 2, the system of Example 1 is optionally configured so that the display includes at least one of an indication of a frequency or a severity of CHF decompensation events that are included in the physiological data.

In Example 3, the system of at least one of Examples 1-2 is optionally configured so that the display includes a graphical or tabular representation of a metric relating to a false negative versus a metric relating to a false positive characterizing the multiple algorithm variations.

In Example 4, the system of at least one of Examples 1-3 is optionally configured so that the display is in the form of a receiver operating characteristic (ROC).

In Example 5, the system of at least one of Examples 1-4 is optionally configured so that the population data selector includes a criterion of physiological similarity to the first patient for selecting a candidate different second patient, wherein the criterion includes at least one of age, gender, ethnicity, left ventricular ejection fraction, New York Heart Association heart failure classification, six minute walk test results, a quality of life measure, a heart failure etiology, a body mass index, a blood pressure, a medication, a co-morbidity, an arrhythmia history, an implant history, a patient treatment compliance, a health care system, a circadian rhythm, a geographic location, patients who have survived for a particular time frame, and patients who have not decompensated or experienced other cardiac events in a particular time frame.

In Example 6, the system of at least one of Examples 1-5 is optionally configured so that the multiple algorithm variations include multiple variations of at least one of a CHF detection algorithm, a CHF classification algorithm, or a CHF prediction algorithm.

In Example 7, the system of at least one of Examples 1-6 is optionally configured so that the local or remote external user interface accepts user input limiting values for the implantable physiological data to a particular range of values.

In Example 8, the system of at least one of Examples 1-7 is optionally configured so that the implantable medical device includes at least one of an implantable cardiac defibrillator, a cardiac resynchronization therapy device, and a pacer.

In Example 9, the system of at least one of Examples 1-8 is optionally configured so that the implantable medical device measures at least one of a heart sound, a heart rate, a heart rate turbulence, a heart rate variability, a pulmonary artery pressure, an electrogram morphology, a blood pressure, a thoracic impedance, a respiration rate, and a heart failure index.

In Example 10, the system of at least one of Examples 1-9 is optionally configured so that the physiological data input comprises an external physiological data input configured to receive external physiological data from an external physiological sensor associated with, but external to, the first patient, and wherein the external physiological data includes at least one of a body weight, a systolic blood pressure, a diastolic blood pressure, a response to health symptoms questions, and a glucose level.

In Example 11, the system of at least one of Examples 1-10 is optionally configured so that the multiple algorithm variations include at least one of an alteration of algorithm program code or an alteration of an algorithm parameter.

In Example 12, the system of at least one of Examples 1-11 is optionally configured so that the processor automatically reprograms the implantable medical device with an algorithm selected from the multiple algorithm variations.

In Example 13, the system of at least one of Examples 1-12 is optionally configured so that the processor automatically programs the implantable medical device as a function of an area under a receiver operator characteristic curve.

In Example 14, the system of at least one of Examples 1-13 is optionally configured so that the processor programs the implantable medical device as a function of a false positive rate and a sensitivity.

In Example 15, the system of at least one of Examples 1-14 is optionally configured so that the processor receives input from a user for selecting an algorithm from the multiple algorithm variations to program into the implantable medical device.

Example 16 describes a process comprising receiving, at a physiological data input of a remote external server, physiological data into a patient data storage device that stores historical physiological data of a population of congestive heart failure (CHF) patients, wherein the physiological data input comprises an implantable physiological data input configured to receive implantable physiological data from an implantable physiological sensor of a first patient; applying multiple algorithm variations against the same implantable physiological data from the first patient to produce corresponding resulting CHF indicators; and displaying, on a local or remote user interface, a comparison between the resulting CHF indicators from the multiple algorithm variations, and displaying, on the local or remote user interface, a population data selector configured to permit the user to select physiological data from a different set of one or more patients or physiological data collected over a period of time from the first patient; and optimizing an algorithm parameter or a selection of a best performing algorithm as a function of the multiple algorithm variations.

In Example 17, the process of Example 16 is optionally configured for displaying on the local or remote user interface at least one of an indication of a frequency or a severity of CHF decompensation events that are included in the physiological data.

In Example 18, the process of at least one of Examples 16-17 is optionally configured for displaying includes a graphical or tabular representation of a metric relating to a false negative versus a metric relating to a false positive characterizing the multiple algorithm variations.

In Example 19, the process of at least one of Examples 16-18 is optionally configured for displaying on the local or remote user interface is in the form of a receiver operating characteristic (ROC).

In Example 20, the process of at least one of Examples 16-19 is optionally configured for providing an option to select one or more values for at least one tunable algorithm parameter as a function of receiver operating characteristic information.

In Example 21, the process of at least one of Examples 16-20 optionally configures the local or remote user interface to accept user input limiting values of the implantable physiological data to a particular range of data.

In Example 22, the process of at least one of Examples 16-21 optionally configures the physiological data input to receive external physiological data from an external physiological sensor associated with the first patient.

In Example 23, the process of at least one of Examples 16-22 is optionally configured for automatically reprogramming the implantable medical device with an algorithm automatically selected from the multiple algorithm variations.

In Example 24, the process of at least one of Examples 16-23 is optionally configured for receiving input from a user relating to an algorithm to select from the multiple algorithm variations to program into the implantable medical device.

Example 25 describes a system for use with an implantable medical device, the system comprising remote external server means, comprising physiological data input means, configured to receive physiological data into a patient data storage device that stores historical physiological data of a population of congestive heart failure (CHF) patients, the physiological data input means comprising an implantable physiological data input, configured to receive implantable physiological data from an implantable physiological sensor of a first patient; processor means, coupled to the patient data storage device, the processor means configured to apply multiple algorithm variations against the same implantable physiological data from the first patient to produce corresponding resulting CHF indicators; and local or remote external user interface means, configured to be coupled to the remote external server means using a communications network, the user interface comprising a display means, configured to display to a user information allowing comparison between the resulting CHF indicators from the multiple algorithm variations, and the display means including a population data selector configured to permit the user to select physiological data from a population comprising a different set of one or more patients or physiological data collected over a period of time from the first patient, thereby further allowing an optimization of an algorithm parameter or a selection of a best performing algorithm.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8 is a table of example predictions for a Receiver Operator Characteristic space.

DETAILED DESCRIPTION

Figure 1:
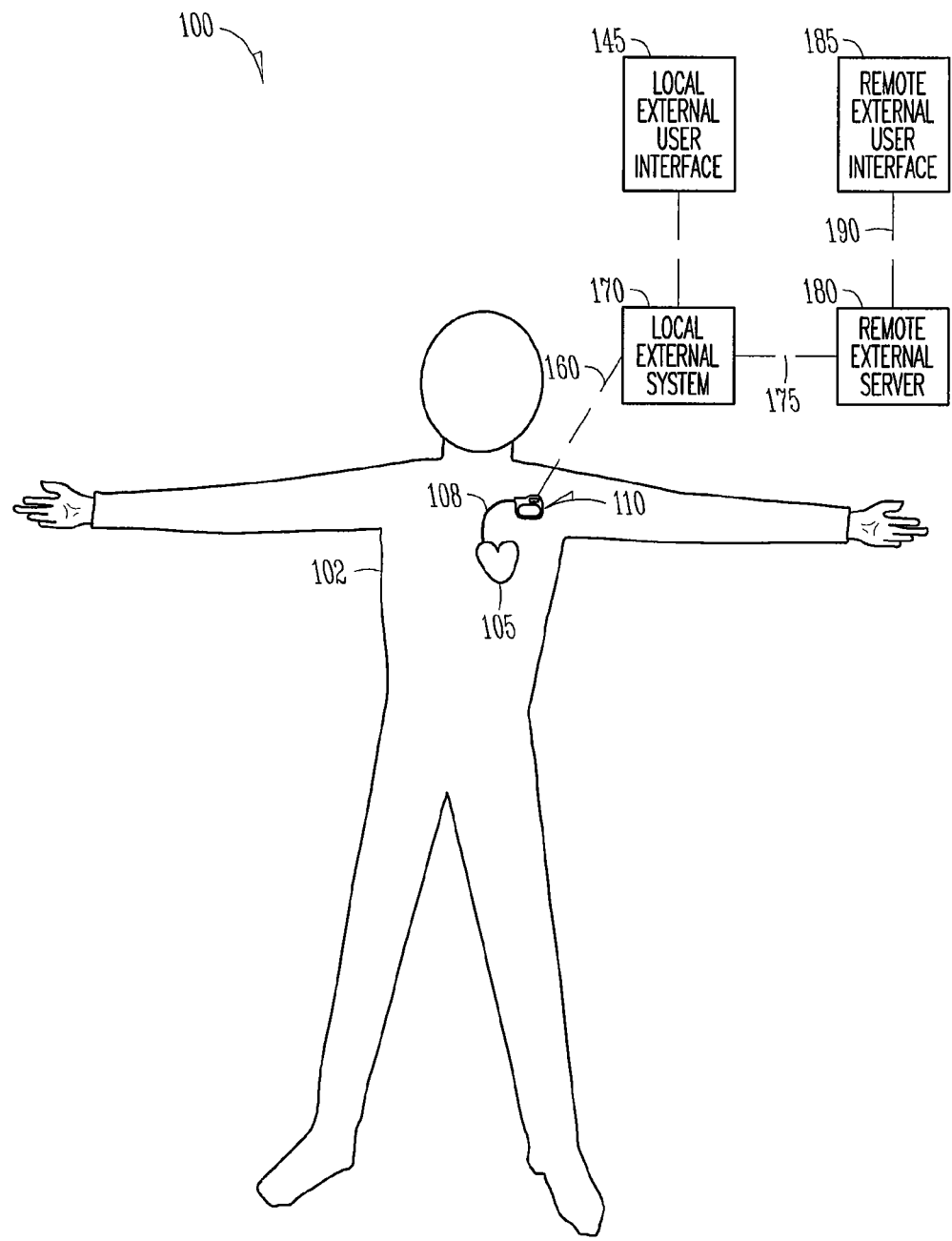
FIG. 1 illustrates an example of an implanted medical device in communication with external devices via a telemetry system.

FIG. 1 is a diagram illustrating an example of a medical device system 100, and portions of an environment in which it is used. The environment includes a body 102 with a heart 105. In this example, the system 100 includes an implantable medical device 110, a lead system 108, a local external user system 170, a local external user interface 145, a remote external server 180, a remote external user interface 185, and a wireless telemetry link 160. The implantable medical device 110 can include at least one of an implantable cardiac defibrillator, a cardiac resynchronization therapy device, or a pacer. The system 100 can be a leadless system that does not have the lead system 108. The local external user system 170 can be coupled to the remote external server 180 via a wired or wireless communications link 175. The remote external user interface 185 can be coupled to the remote external server 180 via a wired or wireless link 190. Heart rate or other physiological data, therapy delivery data (such as pacing data or drug titration data), electrogram data, hemodynamic data, heart sound data, heart rate turbulence data, heart rate variability data, pulmonary artery pressure data, thoracic or intracardiac impedance data, a heart failure index, or other data can be transferred from the device 110 to the local external user system 170 via the telemetry link 160. The telemetered data loaded into the local external user system 170 can then be used for analysis and interpretation either immediately or at a later time. The data in the local external user system 170 can also be transmitted to the remote external server 180 through link 175 which can include a repeater, a computer or communications network, or the like.

Figure 2:
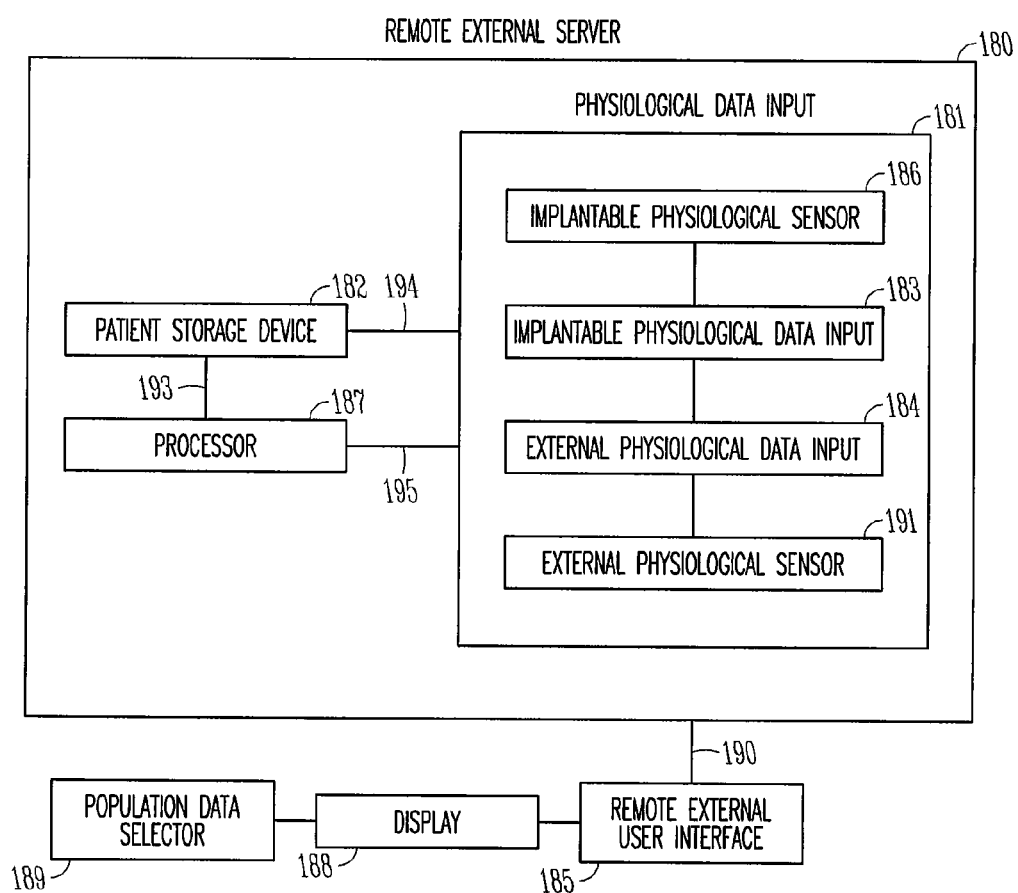
FIG. 2 illustrates an example of the remote server of FIG. 1.

FIG. 2 illustrates an example of the remote external server 180 in greater detail. In this example, the remote external server 180 includes a physiological data input 181 and a patient storage device 182. The physiological data input 181 includes an implantable physiological data input 183. The physiological data input 181 can also include an external physiological data input 184 that is external to, although associated with, a patient in whom a medical device is implanted. The implantable physiological data input 183 is coupled to an implantable physiological sensor 186. In an example, the implantable physiological sensor 186 is part of the implantable device 110. In an example, the implantable physiological sensor 186 is a stand alone sensor. The remote server 180 includes a processor 187. The processor 187 is coupled to the patient storage device 182 via a link 193. A remote external user interface 185 is coupled to the remote external server 180 via a link 190. The physiological data input 181 can be coupled to the patient storage device 182 and the processor 187 via links 194 and 195 respectively.

In an example, the physiological data input 181 of the remote external server 180 is configured to receive physiological data from the implantable medical device 110 or the implantable physiological sensor 186. The physiological data can be stored in the patient data storage device 182. The patient storage device 182 can further store data relating to a population of congestive heart failure (CHF) patients. The processor 187 can be configured to apply multiple algorithm variations against the same implantable physiological data from a patient to produce corresponding resulting CHF indicators. The multiple algorithm variations can include multiple variations of at least one of a CHF detection algorithm, a CHF classification algorithm, or a CHF prediction algorithm. The remote external user interface 185 can be configured to be coupled to the remote external server 180 using a communications network. A display 188 associated with the remote external user interface 185 can be configured to display to a user information that allows the user to compare the resulting CHF indicators from the multiple algorithm variations. The display can further include a population data selector 189 configured to permit the user to select physiological data from a population in the patient database 182. The population physiological data can include data from a set of one or more patients or physiological data collected over a period of time from the patient in whom the medical device is implanted. The user can then, as described in further detail below, select or optimize one or more algorithm parameters, or the user can select out of a plurality of algorithms an algorithm that performs the best based on the execution of the algorithms using the population physiological data or the patient's own historical data. The system can also be configured to automatically select the parameters or algorithm that give the particularly desirable results.

The display 188 can be configured to display several types of information, and in particular, several types of CHF decompensation data. For example, the display 188 can include an indication of a frequency or severity of CHF decompensation events that are included in the physiological data. The frequency can be displayed on a daily, weekly, monthly, or other time period basis. The severity can be indicated by any number of CHF indicators such as ejection fraction, as an illustrative example.

In certain examples, one or more algorithms yields a diagnostic or classification decision or the like. In these or other examples, the display can further include a graphical or tabular representation of a metric relating to a false negative against a metric relating to a false positive, such as characterizing the multiple algorithm variations. In an example, the display is in the form of a receiver operating characteristic (ROC) curve.

For example, if a physician or other care provider has access to past clinical events in addition to physiologic sensor data for a patient (either from the patient alone or from a population of patients with similar clinical conditions), the physician can replay a particular patient management algorithm over all past data, and create an ROC curve that would summarize the performance of the algorithm over the dataset. The physician could also use the past data in replays of an algorithm variation, such as an altered patient management algorithm (e.g., altered program code or altered program parameters), and determine the particular algorithm variation that generates the best performance (e.g., based on a False Positive Rate (FPR) or a sensitivity measure).

Figure 3:
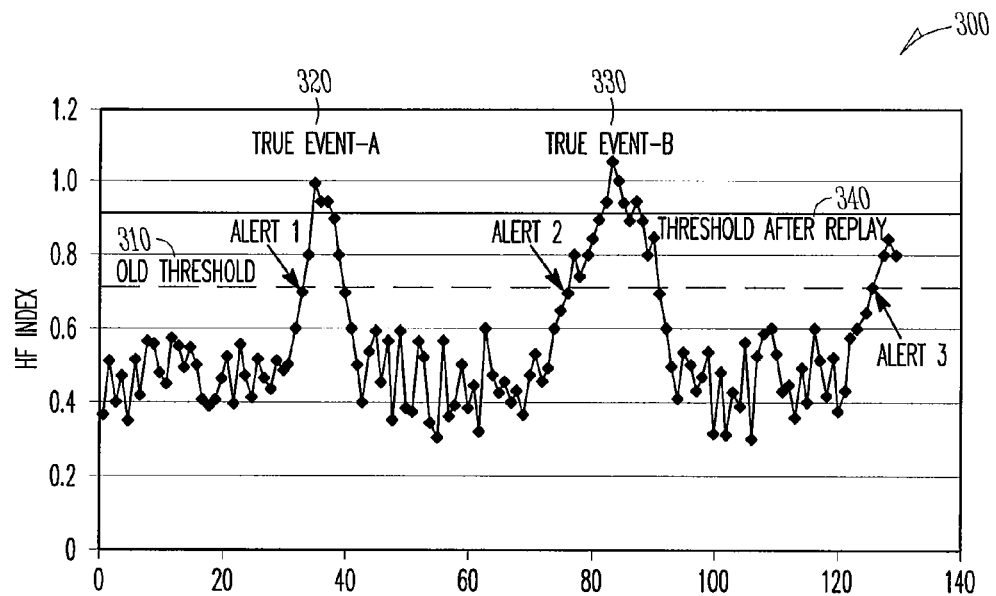
FIG. 3 illustrates an example of a relationship between cardiac events and one or more thresholds.

FIG. 3 illustrates an example 300 of a trend of a HF index such as can be created from one or a composite of device-based or external HF sensors. The algorithm on a remote server such as remote external server 180 can apply a fixed threshold on the HF index trend to determine a HF decompensation alert. When the HF index increases above the threshold, the algorithm declares a HF decompensation event alert. The dotted line shows a current threshold 310. The current threshold 310 can be suggested or specified, such as by the remote external server 180 (e.g., based on an evaluated performance on a population) and can be programmable by the clinician or automatically.

Using a combination of data from a patient's implantable medical device 110 and the patient storage device 182, a clinician has access to retrospective data specific to his or her patient. The clinician also has access to clinical events retrospectively through electronic medical records in the patient storage device 182. From this data, the clinician can determine that the patient had two decompensation events marked A (320) and B (330), in this illustrative example. The clinician can apply the current algorithm threshold over the retrospective patient data to assess the performance and decide the desired threshold for the patient, which as illustrated in FIG. 3, may be changed from the old threshold at 310 to a new threshold 340 after the replay of data.

As seen in the illustrative example of FIG. 3, the algorithm in the implantable medical device declares three alerts—Alert 1, Alert 2, and Alert 3—because the HF index crosses the threshold 310. Thus, the performance of the implantable medical device algorithm can be summarized as generating two true positives, one false positive, and no false negatives.

Since the algorithm can be replayed at any time over any time period, it is uncertain how often an absence of an event will be detected. Therefore, for an algorithm of this nature, a false positive rate (FPR) is a likely a more useful performance metric than specificity. In FIG. 3, since there was one false positive in 125 days, the false positive rate can be calculated as (365/125)×1=2.92 false events/man-year. Thus the performance can be summarized as having a sensitivity of 100% (2/2) and a false positive rate of 2.92 false positives per man year. Moreover, replaying patient and population data in an implantable medical device algorithm over a range of thresholds can generate a value of sensitivity and a false positive rate for each threshold.

Figure 4:
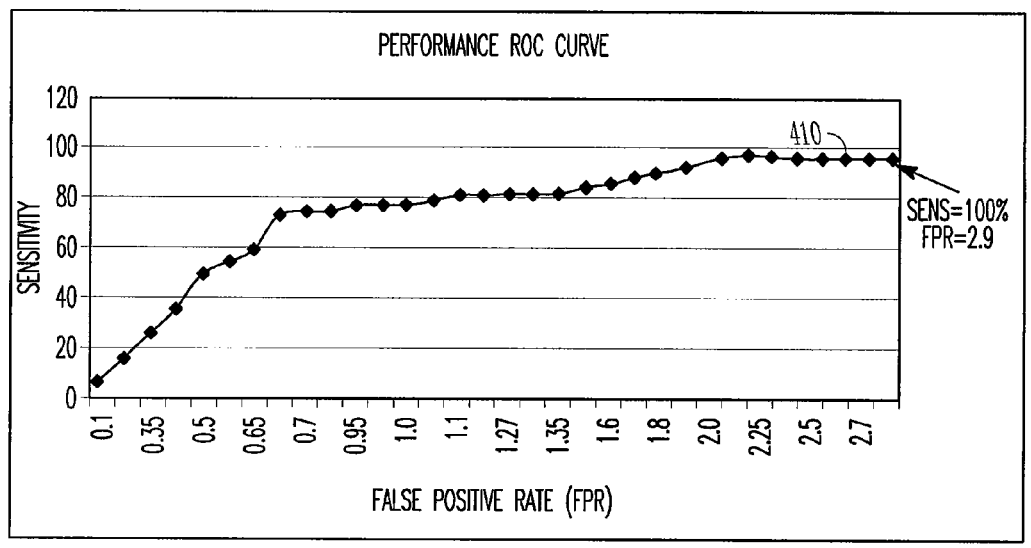
FIG. 4 illustrates an example of a Receiver Operator Characteristic (ROC) curve.

The display system 188 allows a physician or other health care provider to move the threshold 310 up or down and summarize the algorithm performance using various different values of the threshold 310. In the example of FIG. 3, the physician can program the system to the threshold 340 in order to avoid the false alert 3 without lowering the sensitivity. Thus, at every threshold value, a new value of sensitivity and false positive rate can be obtained. This performance can be also summarized using an ROC curve as shown in FIG. 4. In FIG. 4, each point on the curve 410 represents use of a certain threshold value, such as a threshold value from a plot like FIG. 3, that would give a sensitivity and False Positive Rate (FPR) as indicated on FIG. 4. A physician can then choose the desired FPR and sensitivity by selecting a point of the ROC curve. In certain examples, the corresponding algorithm can be automatically selected based on a physician specified FPR or sensitivity.

The display 188 can display data as in FIG. 3 along with clinical labels indicating whether an algorithm-declared event is a true event. Whether an event is a true event can be specified by a clinician. A clinician can change these labels based on the clincian's knowledge of the patient and patient data. The display 188 can also display a current threshold 310 and new threshold 340, and can permit the physician to move the thresholds on the display 188. Also, performance metrics for the current threshold 310 and the newly selected threshold 340 can be displayed. The ROC curve such as the curve 410 in FIG. 4 can depict the range of performance metrics for various threshold levels.

A ROC curve such as the curve illustrated in FIG. 4 can be a graphical plot of the sensitivity against (1−specificity) for a binary classifier system as its discrimination threshold is varied. The ROC curve can also be represented by plotting a fraction of true positives (TPR=true positive rate) against a fraction of false positives (FPR=false positive rate).

For example, in a two-class prediction problem (binary classification), the outcomes can be labeled either as a positive (p) or a negative (n) class. There are four possible outcomes from a binary classifier. If the outcome from a prediction is p and the actual value is also p, then it is called a true positive (TP); however if the actual value is n then it is said to be a false positive (FP). Conversely, a true negative occurs when both the prediction outcome and the actual value are n, and a false negative is when the prediction outcome is n while the actual value is p. For example, a diagnostic test may determine whether a person is positive or negative for a certain disease. A false positive in this case occurs when the patient tests positive, but does not have the disease. A false negative, on the other hand, occurs when the person tests as healthy when in fact the person has the disease.

In an example, an experiment can be defined as having P positive instances and N negative instances. The four outcomes can be formulated in a 2×2 confusion matrix or contingency table, as follows:

| | | Actual Outcome | |
|---|---|---|---|
| Prediction | P' | True Positive | False Positive |
| Outcome | N' | False Negative | True Negative |
| | Total | P | N |

Terminology and derivations:
    true positive (TP)—correct detection
    true negative (TN)—correct rejection
    false positive (FP)—incorrect detection (Type I error)
    false negative (FN)—incorrect rejection (Type II error)
    true positive rate (TPR)—sensitivity $$TPR = TP/P = TP/(TP+FN)$$

false positive rate (FPR)—false alarm rate $$FPR = FP/N = FP/(FP+TN)$$

accuracy (ACC)

$$ACC = (TP+TN)/(P+N)$$

specificity (SPC)

$$SPC = TN/(FP+TN) = 1 - FPR$$

positive predictive value (PPV)

$$PPV = TP/(TP+FP)$$

negative predictive value (NPV)

$$NPV = TN/(TN+FN)$$

From the confusion matrix, several evaluation metrics can be derived as illustrated above. To generate an ROC curve, only the true positive rate (TPR) and the false positive rate (FPR) are needed. The TPR determines a classifier or a diagnostic test performance on classifying positive instances correctly among all positive samples available during the test. The FPR, on the other hand, defines the number of incorrect positive results among all negative samples available during the test.

An ROC space can be defined by the FPR and the TPR as x and y axes respectively, which depicts relative trade-offs between true positive (benefits) and false positive (costs). Since the TPR can represent sensitivity and the FPR can represent (1−specificity), the ROC curve can be referred to as a sensitivity versus (1−specificity) plot. Each prediction result or instance of a confusion matrix represents one point in the ROC space.

Figure 5:
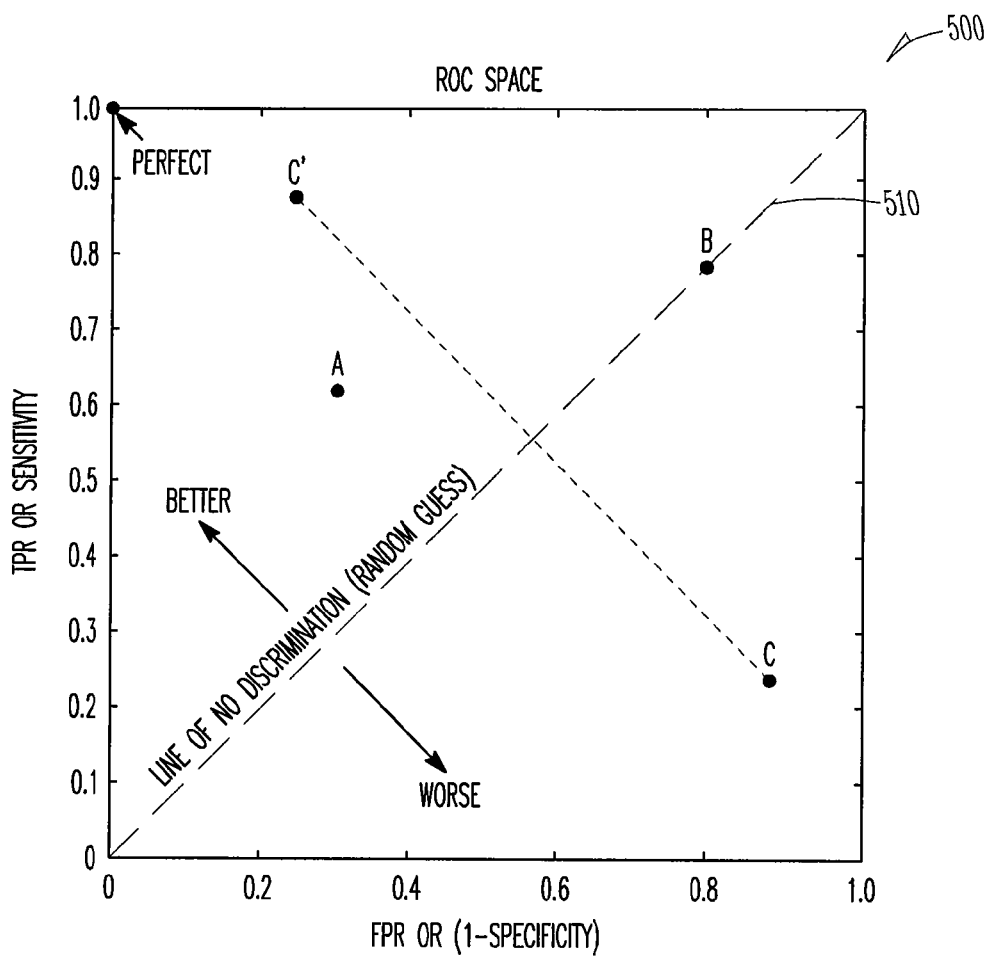
FIG. 5 illustrates an example of a Receiver Operator Characteristic space.

An example of an ROC space is illustrated in FIG. 5. The best possible prediction method would yield a point in the upper left corner or coordinate (0,1) of the ROC space 500, representing 100% sensitivity (all true positives are found) and 100% specificity (no false positives are found). The (0,1) point can also be called a perfect classification. A completely random guess would give a point along a diagonal line 510 (the so-called line of no-discrimination) from the left bottom to the top right corners. The diagonal line 510 determines which area indicates good or bad classification or diagnostic results. Points above the diagonal line 510 indicate good classification results, while points below the line indicate incorrect results. For example, FIG. 8 illustrates four prediction results from 100 positive and 100 negative instances. Plots of the four prediction results from FIG. 8 in the ROC space 500 are given in FIG. 5. The result A clearly shows the best among B and C. However, when C is mirrored onto the diagonal line, as seen in C', the result is better than A. The result B lies on the random guess line (the diagonal line 510), and it can be seen from the above table that the accuracy of B is 50%.

An ROC curve can be used to generate a summary statistic. Examples include the intercept of the ROC curve with a line at 90 degrees to the no-discrimination line, an area between the ROC curve and the no-discrimination line, and an area under the ROC curve. The area under the ROC curve can represent a difference in median between scores of two groups.

The area under the ROC curve is a convenient and useful way of comparing classifiers, that is, determining which implantable medical device algorithm or set of parameters is optimal. A single ROC curve can inform which operating point is optimal, or an area under a segment of an ROC curve that corresponds to a particular range of values can be used. A classifier can be used by choosing an operating point, that is, a threshold. This fixes a point on the ROC curve. In some cases the area may be misleading. That is, when comparing classifiers, the one with the larger area may not be the one with the better performance at the chosen threshold (or limited range). Usually a classifier is used at a particular sensitivity, or at a particular threshold. The ROC curve can then be used to choose the desired operating point, for example, the best operating algorithm in an implantable medical device. The desired operating point might be chosen so that the classifier gives the best trade off between the costs of failing to detect positives against the costs of raising false alarms. These costs need not be equal, but equal costs can be assumed, if desired.

If the costs associated with classification are a sum of the cost of misclassifying positive and negative cases, then all points on a straight line (whose gradient is given by the importance of the positive and negative examples) have the same cost. If the cost of misclassifying positive and negative cases are the same, and positive and negative cases occur equally often, then the line has a slope of 1 (e.g., 45 degrees). A desirable place to operate the classifier is the point on its ROC curve which lies on the 45 degree line closest to the north-west corner (0,1) of the ROC curve.

In an example, the average expected cost of classification at a point x,y in the ROC space can be calculated as follows:

$$C=(1-p)\text{alpha } x+p \text{ beta}(1-y)$$

wherein alpha represents the cost of a false positive (false alarm), beta represents the cost of missing a positive (false negative), and p represents the proportion of positive cases. Isocost lines (lines of equal cost) are parallel and straight, and their gradients depends upon alpha/beta and (1−p)/p. (Actually the gradient=alpha/beta times (1−p)/p). If costs are equal (alpha=beta) and 50% are positive (p=0.5), the gradient is 1 and the isocost lines are at 45 degrees.

In an example, a user can choose a population data selector 189 to compare a patient with an implanted device with one or more other patients. This selector can be chosen on the basis of some physiological or other similarity between the patient and the one or more other persons from the population. For example, physiological population data selectors can include one or more of age, gender, ethnicity, left ventricular ejection fraction, New York Heart Association heart failure classification, results from walking or other physical tests, a quality of life measure, a heart failure etiology, a body mass index, a blood pressure, an arrhythmia history, or a circadian rhythm. Other population data selectors can include medication data, co-morbidity data, an implant history, patient compliance with treatment schedules and protocols, a common or different health care system, a common or different geographic location, patient survival rates and durations, and patient decompensation histories.

The remote external user interface 185 or the local external user interface 145 can be configured to accept input from a user that limits values for the implantable physiological data to a particular range of values. For example, if the physiological data of concern is heart rate, the user can limit the heart rate data to either above or below a particular heart rate, or heart rate data that falls between a lower heart rate limit and an upper heart rate limit. Other physiological data that could be measured by the implantable device, and consequently limited by a user through one or more of the interfaces 185 or 145 include a heart sound, a heart rate turbulence, a heart rate variability, a pulmonary artery pressure, an electrogram morphology, a blood pressure, a thoracic impedance, a respiration rate, and a heart failure index. For example, heart sound data could be limited to a particular heart sound such as the S3 heart sound, or it could be limited to heart sounds of a particular frequency or amplitude. Other physiological data could be limited by a user through the user interface in a similar manner. Similarly, physiological data can be collected by the external physiological data input 184 that is configured to receive external physiological data from an external physiological sensor 191. The data that can be collected by the external physiological sensor 191, and thus can be selected by a user, include a body weight, a systolic blood pressure, a diastolic blood pressure, a response to health symptoms questions, and a glucose level.

In an example, the multiple algorithms that are associated with the implantable medical device can be generated by either an alteration of the algorithm code or parameters that are supplied to the algorithm. After the replay of data from either the population of patient data, or the historical patient data of the patient under treatment, the processor 187 can be configured to automatically reprogram the implantable medical device with an algorithm selected from the multiple algorithm variations (algorithm code variations or algorithm parameter variations). This automatic selection can be accomplished through the use of the ROC as explained above, such as by programming into the system the desired FPR and sensitivity, and configuring the system to select the point of an ROC curve corresponding to the FPR and sensitivity. The processor 187 can also be configured to receive input from a user through one of the user interfaces 145 or 185 for selecting an algorithm from the multiple algorithm variations to program into the implantable medical device.

Figure 6:
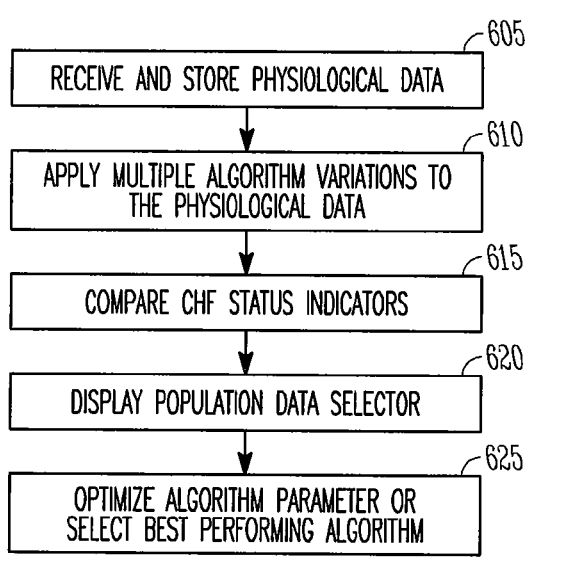
FIG. 6 illustrates an example process to optimize parameters for an algorithm of an implantable medical device or select a best performing algorithm for an implantable medical device.

FIG. 6 illustrates an example process 600 that replays data collected either from an implantable medical device over a period of time, or replays data collected from a population of individuals. An algorithm, a portion of an algorithm, or parameters associated with the algorithm, can be altered between the replays of the algorithm. At 605, physiological data are received at a physiological data input and stored in a patient storage device. The patient storage device can also store historical physiological data of a population of congestive heart failure patients. The physiological input of operation 605 can include an implantable physiological data input that is configured to receive implantable physiological data from an implantable physiological sensor associated with a patient.

At 610, multiple algorithm variations are applied against the same implantable physiological data from the patient, and corresponding CHF indicators are generated. At 615, a comparison is displayed between the resulting CHF indicators generated by the multiple algorithm variations on a local or remote user interface. At 620, a population data selector is displayed on the local or remote user interface. The population data selector is configured to permit a user to select physiological data from a different set of one or more patients or physiological data collected over a period of time from the patient with the implantable medical device. At 625, an algorithm parameter is optimized or a best performing algorithm is selected as a function of the multiple algorithm variations.

Figure 7:
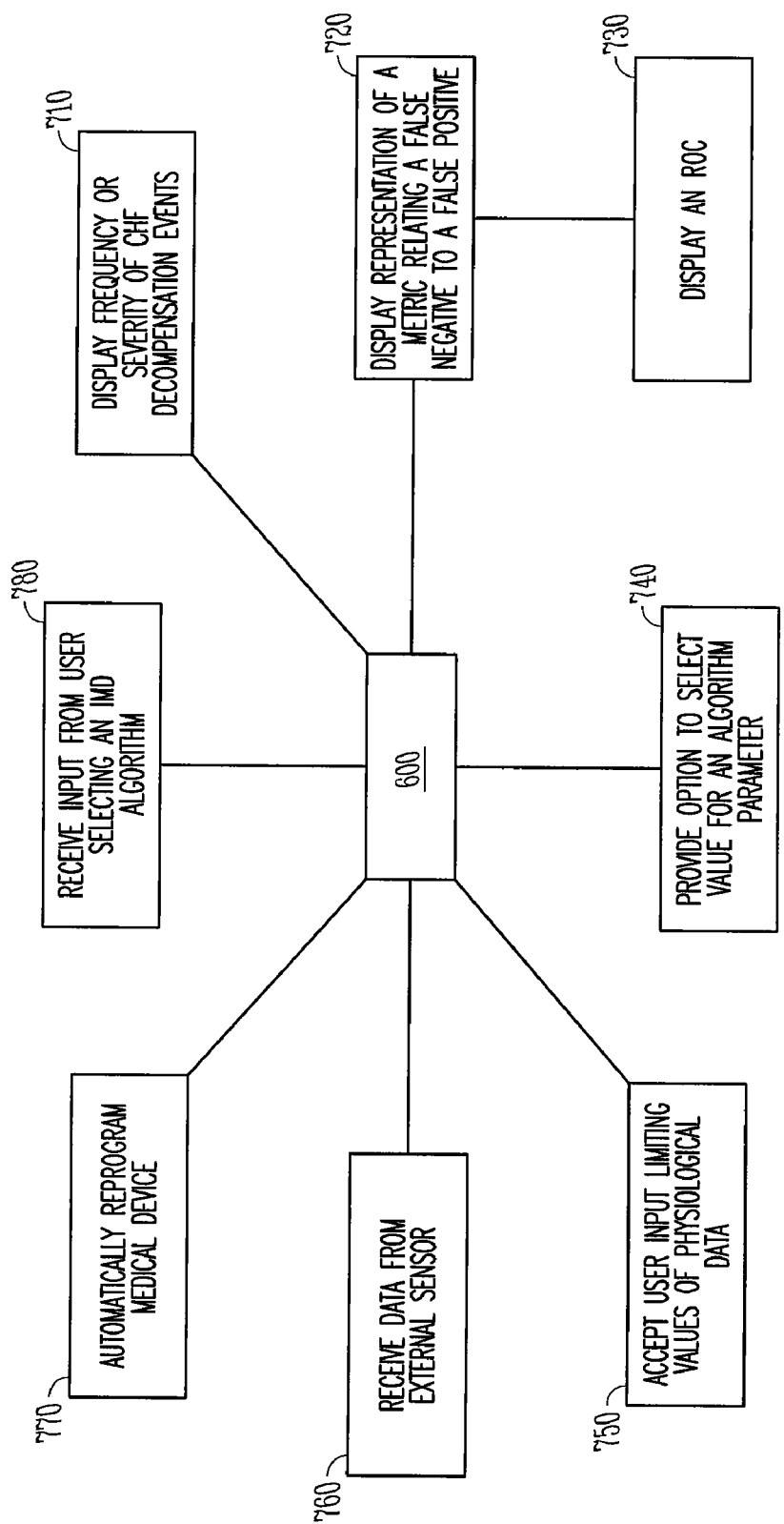
FIG. 7 illustrates several example functions that can be implemented in connection with the process of FIG. 6.

FIG. 7 illustrates examples of additional operations that can be included in association with the process 600 of FIG. 6. At 710, an indication of a frequency or severity of CHF decompensation events that are included in the physiological data is displayed on the local or remote user interface. At 720, a graphical or tabular representation of a metric relating to a false negative versus a metric relating to a false positive characterizing the multiple algorithm variations is displayed. At 730, an ROC is displayed on the local or remote user interface. At 740, an option to select one or more values for at least one tunable algorithm parameter as a function of receiver operating characteristic information is provided. At 750, the local or remote user interface is configured to accept user input limiting values of the implantable physiological data to a particular range of data. At 760, the physiological data input is configured to receive external physiological data from an external physiological sensor associated with the first patient. At 770, the implantable medical device is automatically reprogrammed with an algorithm automatically selected from the multiple algorithm variations. At 780, input is received from a user relating to an algorithm to select from the multiple algorithm variations to program into the implantable medical device.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system for use with an implantable medical device, the system comprising:
   a remote external server, comprising:
      a physiological data input, configured to receive physiological data into a patient data storage device that stores historical physiological data of a population of congestive heart failure (CHF) patients, the physiological data input comprising an implantable physiological data input configured to receive implantable physiological data from an implantable physiological sensor of a first patient;
      a processor, coupled to the patient data storage device, the processor configured to apply multiple algorithm variations against the same implantable physiological data from the first patient to produce corresponding resulting CHF indicators; and
   a local or remote external user interface, configured to be coupled to the remote external server using a communications network, the local or remote external user interface comprising a display, configured to display to a user information allowing comparison between the resulting CHF indicators from the multiple algorithm variations, and the display including a population data selector configured to permit the user to select physiological data from a population comprising a different set of one or more patients or physiological data collected over a period of time from the first patient,
   wherein the processor is configured to automatically reprogram the implantable medical device with an algorithm selected from the multiple algorithm variations as a function of a false positive rate and a sensitivity.

2. The system of claim 1, wherein the display includes at least one of an indication of a frequency or a severity of CHF decompensation events that are included in the physiological data.

3. The system of claim 1, wherein the display includes a graphical or tabular representation of a metric relating to a false negative versus a metric relating to a false positive characterizing the multiple algorithm variations.

4. The system of claim 3, wherein the display is in the form of a receiver operating characteristic (ROC).

5. The system of claim 1, wherein the population data selector includes a criterion of physiological similarity to the first patient for selecting a candidate different second patient, wherein the criterion includes at least one of age, gender, ethnicity, left ventricular ejection fraction, New York Heart Association heart failure classification, six minute walk test results, a quality of life measure, a heart failure etiology, a body mass index, a blood pressure, a medication, a co-morbidity, an arrhythmia history, an implant history, a patient treatment compliance, a health care system, a circadian rhythm, a geographic location, patients who have survived for a particular time frame, and patients who have not decompensated or experienced other cardiac events in a particular time frame.

6. The system of claim 1, wherein the multiple algorithm variations include multiple variations of at least one of a CHF detection algorithm, a CHF classification algorithm, or a CHF prediction algorithm.

7. The system of claim 1, wherein the local or remote external user interface is configured to accept user input limiting values for the implantable physiological data to a particular range of values.

8. The system of claim 1, wherein the implantable medical device includes at least one of an implantable cardiac defibrillator, a cardiac resynchronization therapy device, and a pacer.

9. The system of claim 1, wherein the implantable medical device is configured to measure at least one of a heart sound, a heart rate, a heart rate turbulence, a heart rate variability, a pulmonary artery pressure, an electrogram morphology, a blood pressure, a thoracic impedance, a respiration rate, and a heart failure index.

10. The system of claim 1, wherein the physiological data input comprises an external physiological data input configured to receive external physiological data from an external physiological sensor associated with, but external to, the first patient, and wherein the external physiological data includes at least one of a body weight, a systolic blood pressure, a diastolic blood pressure, a response to health symptoms questions, and a glucose level.

11. The system of claim 1, wherein the multiple algorithm variations include at least one of an alteration of algorithm program code or an alteration of an algorithm parameter.

12. The system of claim 1, wherein the processor is configured to receive input from a user for selecting an algorithm from the multiple algorithm variations to program into the implantable medical device.

13. A system for use with an implantable medical device, the system comprising:
a remote external server, comprising:
  a physiological data input, configured to receive physiological data into a patient data storage device that stores historical physiological data of a population of congestive heart failure (CHF) patients, the physiological data input comprising an implantable physiological data input configured to receive implantable physiological data from an implantable physiological sensor of a first patient;
  a processor, coupled to the patient data storage device, the processor configured to apply multiple algorithm variations against the same implantable physiological data from the first patient to produce corresponding resulting CHF indicators; and
a local or remote external user interface, configured to be coupled to the remote external server using a communications network, the local or remote external user interface comprising a display, configured to display to a user information allowing comparison between the resulting CHF indicators from the multiple algorithm variations, and the display including a population data selector configured to permit the user to select physiological data from a population comprising a different set of one or more patients or physiological data collected over a period of time from the first patient, wherein the processor is configured to automatically program the implantable medical device with an algorithm selected from the multiple algorithm variations as a function of an area under a receiver operator characteristic curve.

14. A process comprising:
receiving, at a physiological data input of a remote external server, physiological data into a patient data storage device that stores historical physiological data of a population of congestive heart failure (CHF) patients, wherein the physiological data input comprises an implantable physiological data input configured to receive implantable physiological data from an implantable physiological sensor of a first patient;
applying multiple algorithm variations against the same implantable physiological data from the first patient to produce corresponding resulting CHF indicators; and
displaying, on a local or remote user interface, a comparison between the resulting CHF indicators from the multiple algorithm variations, and displaying, on the local or remote user interface, a population data selector configured to permit the user to select physiological data from a different set of one or more patients or physiological data collected over a period of time from the first patient; and
reprogramming the implantable medical device with an algorithm selected from the multiple algorithm variations as a function of a false positive rate and a sensitivity.

15. The process of claim 14, comprising displaying on the local or remote user interface at least one of an indication of a frequency or a severity of CHF decompensation events that are included in the physiological data.

16. The process of claim 14, wherein the displaying includes a graphical or tabular representation of a metric relating to a false negative versus a metric relating to a false positive characterizing the multiple algorithm variations.

17. The process of claim 16, wherein the displaying on the local or remote user interface is in the form of a receiver operating characteristic (ROC).

18. The process of claim 16, comprising providing an option to select one or more values for at least one tunable algorithm parameter as a function of receiver operating characteristic information.

19. The process of claim 14, comprising configuring the local or remote user interface to accept user input limiting values of the implantable physiological data to a particular range of data.

20. The process of claim 14, comprising configuring the physiological data input to receive external physiological data from an external physiological sensor associated with the first patient.

21. The process of claim 14, comprising automatically reprogramming the implantable medical device with an algorithm automatically selected from the multiple algorithm variations.

22. The process of claim 14, comprising receiving input from a user relating to an algorithm to select from the multiple algorithm variations to program into the implantable medical device.

23. A system for use with an implantable medical device, the system comprising:

means for receiving physiological data into a patient data storage device that stores historical physiological data of a population of congestive heart failure (CHF) patients, wherein the physiologic data includes implantable physiological data from an implantable physiological sensor of a first patient;

means for applying multiple algorithm variations against the same implantable physiological data from the first patient to produce corresponding resulting CHF indicators;

means for displaying, to a user, information allowing comparison between the resulting CHF indicators from the multiple algorithm variations, means for receiving from the user a selection of physiological data from a population comprising a different set of one or more patients or physiological data collected over a period of time from the first patient, and means for updating the implantable medical device with an algorithm selected from the multiple algorithm variations as a function of a false positive rate and a sensitivity.

\* \* \* \* \*